United States Patent [19]
Yamamoto et al.

[11] Patent Number: 5,616,611
[45] Date of Patent: Apr. 1, 1997

[54] α-GLYCOSYL-L-ASCORBIC ACID, AND ITS PREPARATION AND USES

[75] Inventors: Itaru Yamamoto; Norio Muto; Toshio Miyake, all of Okayama, Japan

[73] Assignee: Kabushiki Kaisha Hayashibara Seibutsu Kagaku Kenkyujo, Okayama, Japan

[21] Appl. No.: 805,169

[22] Filed: Dec. 11, 1991

Related U.S. Application Data

[62] Division of Ser. No. 501,899, Mar. 30, 1990, Pat. No. 5,137,723.

[30] Foreign Application Priority Data

May 19, 1989 [JP] Japan ................................ 1-127072
Oct. 20, 1989 [JP] Japan ................................ 1-274518

[51] Int. Cl.$^6$ ..................... A61K 31/375; C07D 307/62
[52] U.S. Cl. ..................... 514/474; 424/400; 514/25; 536/4.1; 536/18.5; 536/18.6; 549/315
[58] Field of Search ............... 514/25, 474; 424/400; 536/401, 18.5, 18.6; 549/315

[56] References Cited

U.S. PATENT DOCUMENTS 4,822,816 4/1989 Markham ................. 514/474
5,084,563 1/1992 Sakai et al. ............... 514/474

FOREIGN PATENT DOCUMENTS 0146121 6/1985 European Pat. Off. .
0033788 12/1964 German Dem. Rep. .
2034315 6/1980 United Kingdom .
8400107 1/1984 WIPO .

OTHER PUBLICATIONS

Chemotherapy of Cancer, 2nd edition, 1981, pp. 361–367, Carter et al.

*Primary Examiner*—Shelley A. Dodson
*Attorney, Agent, or Firm*—Browdy and Neimark

[57] ABSTRACT

α-Glycosyl-L-ascorbic acid exhibiting no direct reducing activity is formed in a solution containing L-ascorbic acid and an α-glucosyl saccharide when subjected to the action of a saccharide-transferring enzyme. α-Glycosyl-L-ascorbic acid is superiorly stable, and readily hydrolyzable in vivo to exhibit the activities inherent to L-ascorbic acid. Thus, α-glycosyl-L-ascorbic acid is favorably useful as a stabilizer, quality-improving agent, antioxidant, physiologically active agent and uv-absorbent in food pharmaceutical and cosmetic industries.

5 Claims, 1 Drawing Sheet

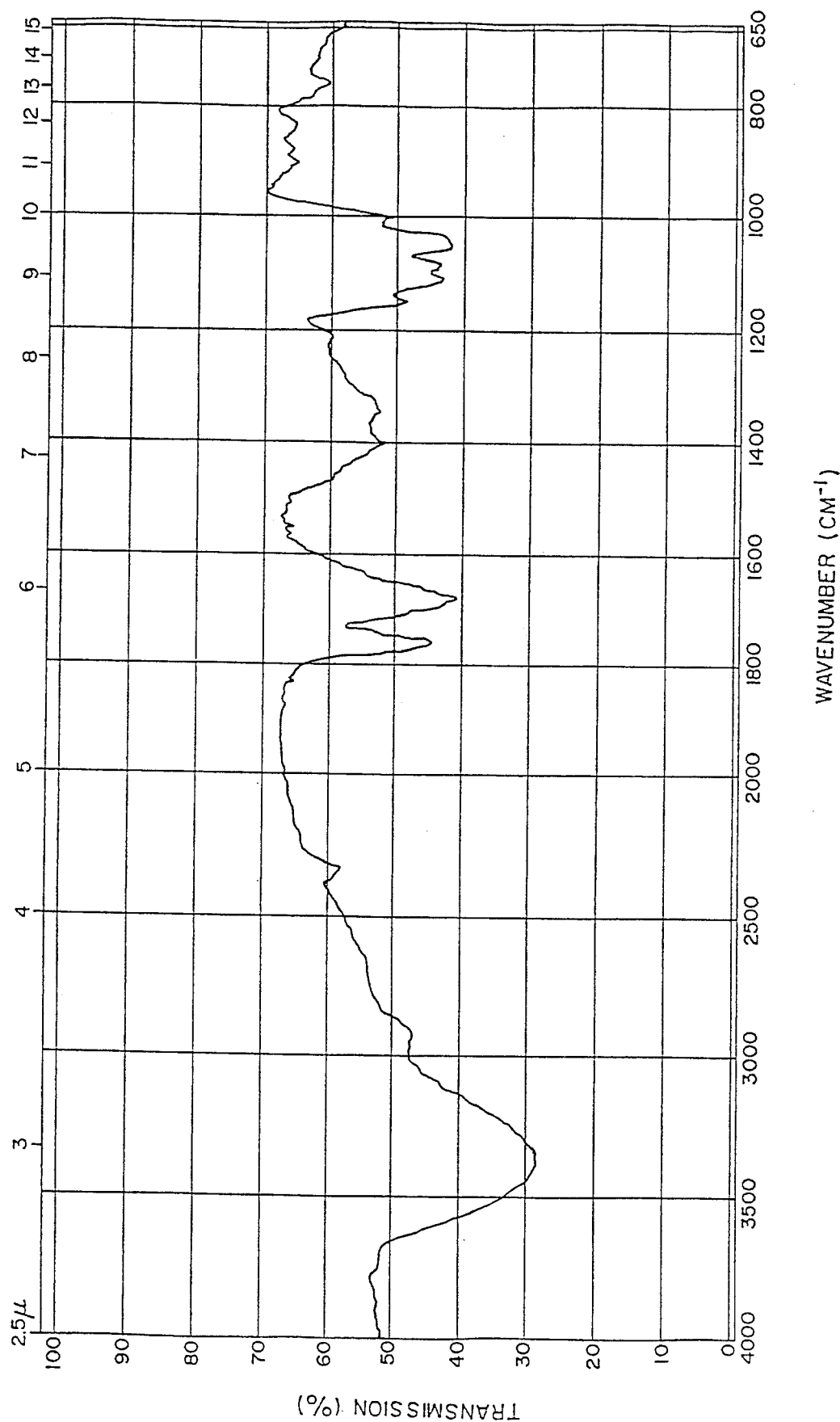

α-GLYCOSYL-L-ASCORBIC ACID, AND ITS PREPARATION AND USES

This is a division of application Ser. No. 07/501,899 filed Mar. 30, 1990 now U.S. Pat. No. 5,137,723.

BACKGROUND OF THE INVENTION

1. Field of the Invention

The present invention relates to an α-glycosyl-L-ascorbic acid exhibiting no direct reducing activity, and its preparation and uses.

More particularly, the present invention relates to a novel substance, an α-glycosyl-L-ascorbic acid exhibiting no direct reducing activity.

The present invention also relates to a biochemical process to prepare the same.

Further, the present invention relates to foodstuffs, tobaccos, pharmaceuticals for susceptive diseases and cosmetics such as beverages, processed foods, preventive and remedy for susceptive diseases, skin-refining agent and skin-whitening agent which all contain the α-glycosyl-L-ascorbic acid.

2. Description of the Prior Art

L-Ascorbic acid, which has the chemical structure shown by the formula [I]:

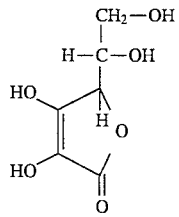

is not synthesized in vivo in human, monkey and guinea pig, therefore is listed as an essential nutritive element, i.e. vitamin C.

L-Ascorbic acid takes part in some physiological activities in vivo; for example, in the hydroxylation of proline and lysine which are necessary to synthesize collagen as the main element of living connective tissues; the oxidation-reduction reaction of cytochrome C wherein $Fe^{+++}$ is reduced into $Fe^{++}$; and in the immunopotentiation via the increase of leukocyte. These are because vitamin C plays a significant role in the maintenance and promotion of health in living body.

Scurvy has been known long as a condition due to deficiency of L-ascorbic acid, and is marked by weakness of the skin, petechial hemorrhage, ecchymosis, and hemorrhages in the gingiva and marrow. To prevent scurvy for the maintenance of health, a recommended daily administration (RDA) is established for L-ascorbic acid; in particular, 60 mg for adult male and 50 mg for adult female.

Nowadays the use of L-ascorbic acid is not limited to agents which enrich vitamin C as an essential nutritive element, but is extending in various applications. More particularly, because of the chemical structure and physiological activities, L-ascorbic acid is useful as a souring agent, reductant, antioxidant, bleaching agent and stabilizer in various chemical reagents, foods and beverages; in pharmaceuticals for susceptive diseases such as preventive and remedy for viral diseases, bacterial diseases and malignant tumors; and further as a reductant, uv-absorbent and melanin-formation inhibitor in cosmetics including skin-refining agent and skin-whitening agent.

The major drawback of L-ascorbic acid is that it readily looses the physiological activities because of its direct reducing activity, poor stability and high susceptibility to oxidation.

To stabilize L-ascorbic acid, some saccharide derivatives of L-ascorbic acid have been proposed. For example, we disclosed in *Vitamin*, Vol. 43, pp. 205–209 (1971), ibid., Vol. 47, pp. 259–267 (1973), and Japanese Patent Publication No. 38,158/73 a biochemical synthesis of L-ascorbic acid glucosides.

Because of the facts that the glucosides are prepared by similar methods; that the formation of an ether bond at the primary alcohol group which is located at the number six carbon atom in L-ascorbic acid leads to the glucosides as described in the Japanese Patent Publication, for example, on the 2nd column, lines 14–16; that the saccharide-transfer reaction from maltose to an α-glucosyl group is responsible for the formation of glucosides; and that the glucosides exhibit a direct reducing activity, their chemical structure would be shown by the formula [II]:

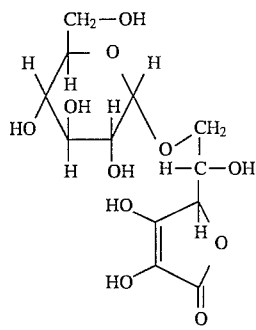

As obvious from the results in the Japanese Patent Publication, the table in Example 1, the stability of the glucosides is superior to that of L-ascorbic acid, but is not enough for their commercialization.

While Ishido et al. disclose in Japanese Patent Publication No. 5,920/83 an organic chemical process to synthesize saccharide derivatives of L-ascorbic acid.

These derivatives are, however, those wherein all the D-glucoses are bound in the β-fashion because up to 21 β-D-glucopyranosyl type derivatives of L-ascorbic acid including 2,3-di-O-(β-D-glucopyranosyl)-L-ascorbic acid are listed for explanation on the 7th column, line 6 to the 8th column, line 11.

Masamoto et al. disclose in Japanese Patent Publication No. 198,498/83 an organic chemical process to synthesize saccharide derivatives of L-ascorbic acid which are also of β-glucosyl type.

Studies on the β-D-glucopyranosyl type derivatives of L-ascorbic acid confirmed that they hardly exhibit desired physiological activities in living body, especially, in human. Furthermore, conventional organic chemical processes have the drawbacks that they are inferior in economical efficiency because the reaction is very complicated and low in yield, as well as that the establishment of non-toxicity and safeness for the resultant derivatives is very difficult.

As described above, the proposals of saccharide derivatives of L-ascorbic acid in the prior art have proved unsatisfactory in view of stability, safeness, physiological activity and economical efficiency, and not been practiced hitherto.

SUMMARY OF THE INVENTION

Accordingly, the realization of a saccharide derivative of L-ascorbic acid which is free from the drawbacks of conventional saccharide derivatives, i.e. superiorly stable, usable without a fear for toxicity, and capable of exhibiting the physiological activities of L-ascorbic acid in vivo, has been in great demand.

The present invention is to overcome the drawbacks of conventional saccharide derivatives of L-ascorbic acid. More particularly, we studied a novel saccharide derivative of L-ascorbic acid which is obtainable by a biochemical process utilizing a saccharide-transfer reaction.

As the result, we discovered a novel saccharide derivative of L-ascorbic acid which is superiorly stable, readily hydrolyzable in vivo, and excellently high in physiological activity, as well as developing its preparation and uses in foods, beverages, cosmetics and pharmaceuticals for susceptive diseases. Thus, we accomplished the present invention.

Since when L-ascorbic acid is ingested with an α-glucosyl saccharide, the α-glycosyl-L-ascorbic acid is readily synthesized and then metabolized, it can be deemed to be a biosubstance, and this is ideally convenient in safeness.

While the β-D-glucosyl type derivatives obtainable by organic chemical processes are not synthesized in vivo, so they would be extraneous to living body.

BRIEF EXPLANATION OF THE FIGURE

FIG. 1 shows the infrared absorption spectrum of the α-D-glucosyl-L-ascorbic acid according to the invention.

DETAILED DESCRIPTION OF THE INVENTION

The present invention is feasible with any α-glycosyl-L-ascorbic acid, regardless of its preparation process such as biochemical and organic chemical processes.

In view of safeness and economical efficiency, desirably, α-glycosyl-L-ascorbic acid is formed by a biochemical process wherein a saccharide-transferring enzyme is allowed to act on a solution containing L-ascorbic acid and an α-glucosyl saccharide.

The wording "exhibiting no direct reducing activity" means that unlike L-ascorbic acid, its saccharide derivative does not reduce and decolor 2,6-dichlorophenolindophenol intact.

The wording "L-ascorbic acid" as referred to in the invention means L-ascorbates such as alkaline metal salts, alkaline earth metal salts and mixtures thereof, and should not be restricted to free L-ascorbic acid, as far as the present invention is feasible therewith. Thus, if necessary, such as sodium L-ascorbate and calcium L-ascorbate are suitably usable in the saccharide-transfer reaction, as well as free L-ascorbic acid.

The wordings "α-glycosyl-L-ascorbic acid" and "2-O-α-D-glucosyl-L-ascorbic acid" mean those in salt form, in addition to those in free acid form, as far as the present invention is feasible therewith.

The α-glucosyl saccharides usable in the invention are those which permit a saccharide-transferring enzyme to form from L-ascorbic acid an α-glycosyl-L-ascorbic acid exhibiting no direct reducing activity. For example, maltooligosaccharides such as maltose, maltotriose, maltoteraose, maltopentaose, maltohexaose, maltoheptaose and maltooctaose are suitably chosen, as well as partial starch hydrolysates such as dextrin, cyclodextrin and amylose, liquefied starch, gelatinized starch, and solubilized starch.

Consequently to facilitate the formation of α-glycosyl-L-ascorbic acid, one should choose an α-glucosyl saccharide which is susceptible to the saccharide-transferring enzyme to be used.

For example, when α-glucosidase (EC 3.2.1.20) is used as the saccharide-transferring enzyme, maltooligosaccharides such as maltose, maltotriose, maltotetraose, maltopentaose, maltohexaose, maltoheptaose and maltooctaose are suitable, as well as partial starch hydrolysates and dextrins with a DE (Dextrose Equivalent) of about 5–60. When cyclomaltodextrin glucanotransferase (EC 2.4.1.19) is used as the saccharide-transferring enzyme, partial starch hydrolysates such as gelatinized starches with a DE below 1 and dextrins with a DE up to 60 are suitable. When α-amylase (EC 3.2.1.1) is used as the saccharide-transferring enzyme, partial starch hydrolysates such as gelatinized starch with a DE below 1 and dextrins with a DE up to about 30 are suitable.

The concentration of L-ascorbic acid during the reaction is generally 1 w/v % or higher, preferably, about 2–30 w/v %, while the concentration of an α-glucosyl saccharide is generally about 0.5- to 30-fold higher than that of L-ascorbic acid.

The saccharide-transferring enzymes usable in the invention are those which transfer one or several α-glucosyl groups at least to the number two carbon atom in L-ascorbic acid without decomposing it when allowed to act on a solution containing L-ascorbic acid and an α-glucosyl saccharide which has an adequate susceptivity to the enzyme.

For example, α-glucosidases derived from animals, plants and microorganisms such as those from mouse kidney, rat intestinal mucosa, dog small intestine, pig small intestine, rice seed, maize seed, and those from a culture which is obtainable by cultivating in a nutrient culture medium yeasts and bacteria of the genera Mucor, Penicillium and Saccharomyces; cyclomaltodextrin glucanotransferases from a culture of bacteria such as those of the genera Bacillus and Klebsiella; and α-amylase from a culture of bacteria such as those of the genus Bacillus are suitably chosen.

Such a saccharide-transferring enzyme should not necessarily be purified prior to its use, as long as it fulfills the above requirements. Generally, the present invention is feasible with a crude enzyme. If necessary, saccharide-transferring enzymes can be purified by conventional method, prior to its use. Of course, commercialized saccharide-transferring enzymes can be used in the invention. The amount of a saccharide-transferring enzyme and reaction time are closely dependent each other. With an economical viewpoint, saccharide-transferring enzyme is used in an amount which completes the reaction within about 3–80 hours.

Immobilized saccharide-transferring enzymes are favorably usable batchwise and in continuous manner.

The reaction process according to the invention is usually carried out by adding a saccharide-transferring enzyme to a solution containing the above described L-ascorbic acid and an α-glucosyl saccharide, and keeping the mixture under conditions where the enzyme is substantially active; usually, at a pH in the range of about 3–9 and a temperature in the range of about 30°–80° C. Since during the reaction L-ascorbic acid tends to cause an oxidative decomposition, it is desirable to keep the mixture under conditions which shield aeration and light as far as possible so that L-ascorbic acid is in its reducing form. The reaction is favorably carried out in the presence of such as thiourea and hydrogen sulfide, if necessary.

The desired substance can be obtained by incorporating L-ascorbic acid and an α-glucosyl saccharide in the culture of a growing microorganism which is capable of producing a saccharide-transferring enzyme.

The α-glycosyl-L-ascorbic acid exhibiting no direct reducing activity will be explained hereinafter. Such a α-glycosyl-L-ascorbic acid bears an α-D-glucosyl group consisting of 1–7 glucosyl groups linked via the α-1,4 fashion, and such an α-D-glucosyl group is bound at least to the primary alcohol group which is located at the number two carbon atom. Particular substances are, for example, 2-O-α-D-glucosyl-L-ascorbic acid, 2-O-α-D-maltosyl-L-ascorbic acid, 2-O-α-maltotriosyl-L-ascorbic acid, 2-O-α-D-maltotetraosyl-L-ascorbic acid, 2-O-α-D-maltopentaosyl-L-ascorbic acid, 2-O-α-D-maltohexaosyl-L-ascorbic acid and 2-O-α-D-maltoheptaosyl-L-ascorbic acid. Although α-glucosidase generally forms only 2-O-α-D-glucosyl-L-ascorbic acid, 2-O-α-D-maltosyl-L-ascorbic acid and 2-O-α-D-maltotriosyl-L-ascorbic acid can be formed in mixture, if necessary.

In the case of using either cyclomaltodextrin glucanotransferase or α-amylase, α-glycosyl-L-ascorbic acids with a higher α-D-glucosyl group are formed in mixture. Dependently on the α-glucosyl saccharide, cyclomaltodextrin glucanotransferase yields an α-D-glucosyl group with a polymerization degree distributing in the range of 1–7, while α-amylase yields a slight narrower distribution. Such a mixture can be partially hydrolyzed with either of α-amylase (EC 3.2.1.1), β-amylase (EC 3.2.1.2) and glucoamylase (EC 3.2.1.3) to reduce the polymerization degree of the α-D-glucosyl group, if necessary. For example, 2-O-α-D-maltosyl-L-ascorbic acid and higher polymers are hydrolyzed to accumulate 2-O-α-D-glucosyl-L-ascorbic acid when subjected to glucoamylase. β-Amylase predominantly hydrolyzes 2-O-α-D-maltotetraosyl-L-ascorbic acid and higher polymers to accumulate 2-O-α-D-glucosyl-L-ascorbic acid, 2-O-α-D-maltosyl-L-ascorbic acid and 2-O-α-D-maltotriosyl-L-ascorbic acid in mixture.

Although a reaction mixture obtained by either of the above methods usually contains the remaining L-ascorbic acid and α-glucosyl saccharide together with an α-glycosyl-L-ascorbic acid which exhibits no direct reducing activity, it can be prepared into final product without no further special treatment. Usually, such a reaction mixture is heated to inactivate the remaining enzyme, filtered and concentrated into a syrupy product which may be then dried and prepared into a powdery product.

When a purified α-glycosyl-L-ascorbic acid product is needed, one can easily isolate an α-glycosyl-L-ascorbic acid in its possible purest form from the contaminants such as remaining L-ascorbic acid, D-glucose and α-glucosyl saccharides by one or more purification methods utilizing the difference in molecular weight and/or affinity; for example, membrane separation, gel filtration chromatography, column chromatography, high-performance liquid chromatography (HPLC) and ion exchange chromatography. In this case, the separated L-ascorbic acid and α-glucosyl saccharide can be favorably reused as a starting material in the saccharide-transfer reaction. If necessary, after completion of the saccharide-transfer reaction but before separation by such as chromatography, the reaction mixture can be treated by one or more methods; for example, a method wherein the reaction mixture is heated and the insolubilized substances are removed by filtration; another method wherein the reaction mixture is treated, for example, with activated carbon to adsorb the proteinaceous and coloring substances for their removal; and one another method wherein the reaction mixture is demineralized with cation exchange resin ($H^+$-form), and treated with anion exchange resin (OH-form) to remove anions and salts by adsorption.

The α-glycosyl-L-ascorbic acid obtained in this way is characterized by:

(1) It exhibits no direct reducing activity, and extremely stable. Unlike L-ascorbic acid, it scarcely causes the Maillard reaction. Because of these, it causes no undesired reaction when mixed with such as protein, lipid, saccharide and physiologically-active substance, but stabilizes these substances.

(2) It is susceptible to hydrolysis to form L-ascorbic acid, and this elicits the same reducing activity as L-ascorbic acid.

(3) It is readily hydrolyzable by the in vivo enzyme system into D-glucose and L-ascorbic acid, and the latter exhibits the physiological activities inherent to L-ascorbic acid.

(4) It is highly safe because it is synthesized and then metabolized in vivo when L-ascorbic acid is ingested together with an α-glucosyl saccharide.

(5) When an α-glycosyl-L-ascorbic acid product additionally contains an α-glucosyl saccharide, the α-glycosyl-L-ascorbic acid exhibits its inherent activities, while the α-glucosyl saccharide exhibits shape-imparting, filling and sweetening effects. Although a product free from α-glucosyl saccharide is low in shape-imparting and filling effects, the inherent effect is attainable with a less amount of the product.

Because of these, the α-glycosyl-L-ascorbic acid exhibiting no direct reducing activity can be favorably incorporated as a stabilizer, quality-improving agent and uv-absorbent, desirably, in an amount of 0.001 w/w % or more, in foods, beverages, preventives and remedies for susceptive diseases including viral diseases, bacterial diseases and malignant tumors, and cosmetics such as skin-refining agents and skin-whitening agents, as well as in agents directed to enrich a highly safe and stable, natural vitamin C.

Since α-glycosyl-L-ascorbic acid is highly resistant to acid, heat and light, and well harmonizes with various substances which taste sour, salty, bitter, delicious and astringent, it is favorably usable as a vitamin C-enriching agent, taste-improving agent, quality-improving agent, stabilizer and antioxidant in foods and beverages in general, for example, seasonings such as soy sauce, say sauce powder, miso, miso powder, "moromi", "hishio", "furikake", mayonnaise, dressing, vinegar, "sanbai-zu", "funmatsu-sushi-su", "chuka-no-moto", "tentsuyu (soup for tenpura)", "mentsuyu (soup for Japanese-style noodles)", Worcester sauce, ketchup, "yakiniku-no-tare (soup for grilled meat)", curry roux, stew premix, soup premix, "dashi-no-moto", mixed seasoning, "mirin (heavily sweetened sake)", "shin-mirin (synthetic mirin)", table sugar and coffee sugar; Japanese-style confectioneries such as "senbei (rice crackers)", "arare (pellet-shaped senbei)", "okoshi (millet-and rice cracker)", "karinto (fried dough cookie)", "gyuhi (starch paste)", rice paste, "manju (bun with a bean-jam filling)", "uiro (sweet rice jelly)", "an (bean jam)", "yokan (sweet jelly of beans)", "mizu-yokan (soft adzuki-bean jelly)", "kingyoku", jelly, castella and "amedama (Japanese-style toffee)"; Western-style confectioneries such as bun, biscuit, cracker, cookie, pie, pudding, cream puff, waffle, sponge cake, doughnut, chocolate, chewing gum, caramel and candy; frozen desserts such as ice cream and sherbet; syrups such as those for fruit preserve and "kaki-gori (shaved ice)"; spreads and pastes such as butter cream, custard cream, flour paste and fruit paste; processed fruits such as jam, marmalade, syrup-preserved fruit and crystallized fruit; processed foods such as those of fruits and vegetables; cereals such as bakery product, noodle, vermicelli, boiled rice and synthetic meat; fatty food substances such as salad oil and margarine; pickled products such as "fukujin-zuke (sliced vegetables picked in soy sauce)", "bettara-zuke (fresh radish pickles)", "senmai-zuke" and "rakkyo-zuke (pickled shallots)"; premixes for pickled products such as "takuan-zuke-no-moto" and "hakusai-zuke-no-moto"; meat products such as ham and sausage; fish meat products such as fish meat ham, fish meant sausage, "kamaboko (boiled fish paste)", "chikuwa (literally bamboo wheels)" and "hanpen"; relishes such as "uni-no-shiokara (salted guts of sea urchin)", "ika-no-shiokara (salted guts of squid)", "su-konbu", "saki-surume", and "fugu-no-mirinboshi"; "tsukudani (food boiled down in soy sauce)" such as those of "nori (dried seaweed)", "sansai (mountain vegetables)", "surume (dried squid)", small fish and shellfish; daily dishes such as "nimame (cooked beans)", potato salad, "konbu-maki (tangle roll)" and "tenpura (deep-fried foods)"; egg and milk products such as "kinshi-tamago", milk beverage, butter and cheese; bottled and canned products such as those of meat, fish meat, fruit and vegetable; alcoholic drinks such as synthetic sake, "zojo shu", liqueur wine and whisky; beverages such as coffee, cocoa, juice, carbonated beverage, lactic acid beverage and lactobacillus beverage; and premixes and instant foodstuffs such as pudding premix, hot cake premix, instant juice, instant coffee, "sokuseki-shiruko (premix of adzuki-bean soup with rice cake)" and instant soup. Furthermore, α-glycosyl-L-ascorbic acid can be favorably incorporated in feeds and pet foods for domestic animals and poultries including honey bee, silkworm and pet fish for the enrichment of vitamin C, the improvement of their taste qualities and the prevention of oxidation.

Also, α-glycosyl-L-ascorbic acid can be favorably incorporated in special foods and beverages, preventives and remedies for susceptive diseases, cosmetics including skin-refining agent and skin-whitening agent, for example, cigar, cigarette, troche, cod-liver oil drop, vitamin compound, oral refreshing agent, cachou, gargle, intubation nutrient, internal medicine, injection, dentifrice, lipstick, eye shadow, milky lotion, moisture liquid, cosmetic cream, foundation, sunscreen agent, cleansing soap, shampoo and rinse, in addition to the uses as uv-absorbent and deterioration-preventing agent for plastics and also as a substrate for assaying glycoside hydrolases.

The wording "susceptive diseases" as referred to in the invention means those which are prevented and/or treated with α-glycosyl-L-ascorbic acid; for example, viral diseases, bacterial diseases, traumatic diseases, immunopathies, allergy, diabetes, cataract and malignant tumors. The shape and form of pharmaceuticals for susceptive diseases can be freely chosen to meet to their final use; for example, liquid pharmaceuticals such as nebula, collyrium, collunarium, collutory and injection, paste pharmaceuticals such as ointment, cataplasm and cream, and solid pharmaceuticals such as powder, granule, capsule and tablet. In the preparation of such a pharmaceutical, one or more ingredients, for example, remedy, biologically-active substance, antibiotic, adjuvant, filler, stabilizer, coloring agent and flavoring agent, can be suitably used in combination, if necessary.

The dose is adequately changed dependently on the α-glycosyl-L-ascorbic acid content, administration route and administration frequency; usually, in the range of about 0.001–100 g/day/adult as α-glycosyl-L-ascorbic acid.

Cosmetics can be prepared similarly as in pharmaceuticals.

α-Glycosyl-L-ascorbic acid is incorporated in products by conventional method, for example, mixing, kneading, dissolving, soaking, spreading, applying, spraying and injecting, before completion of their processing.

When α-glycosyl-L-ascorbic acid and 2-O-α-D-glucosyl-L-ascorbic acid are in free acid form, they can be, if necessary, converted, for example, into sodium salt, calcium salt, magnesium salt, iron salt, copper salt and zinc salt by allowing them to react with an aqueous solution of such as metal hydroxide and metal carbonate so that the resultant substance is capable of adequately adjusting pH and also exhibiting the activities of minerals and vitamin C. Such a substance is favorably usable in nutritive fortifiers and chemical agents.

The following experiments will explain in detail a typical α-glycosyl-L-ascorbic acid exhibiting no direct reducing activity according to the invention.

EXPERIMENT 1

Preparation of α-glucosidase

A fresh rat small intestine was added to 0.1M phosphate buffer (pH 7.0) to 20% by weight, fed to a homogenizer, and centrifuged at 4,000×g for 10 minutes, after which the supernatant was added with a trypsin commercialized by Merck & Co., Inc., Rahway, N.J., USA, to give a final concentration of 0.1 g/l, allowed to stand at ambient temperature for 4 hours, added with 2 volumes of a chilled ethanol, and centrifuged. The sediment was dissolved in 0.01M phosphate buffer (pH 7.0), and the solution was placed in a semipermeable membrane tube, and dialyzed for 15 hours against a fresh preparation of the same buffer.

Thereafter, the liquid inside the tube was chromatographed successively on columns of DEAE-cellulose and hydroxyapatite in usual manner to recover an α-glucosidase-active fraction which was then lyophilized to obtain an α-glucosidase specimen.

The specimen had a specific activity of 40.7 units/mg protein, and the purification degree and activity yield were 357-folds and about 47% respectively.

One unit of α-glucosidase is defined as the amount of enzyme that releases 1 micromole glucose at 37° C. over a time period of 1 minute when assayed under the following conditions. After appropriately diluting, 100 microliters of an enzyme solution is added to a mixture solution of 250 microliters of 4 w/v % maltose and 750 microliters of 0.1M acetate buffer (pH 6.0) containing 1.35 mM EDTA, and the mixture is allowed to react at 37° C. for 30 minutes, incubated in boiling water for 3 minutes to suspend the reaction, and centrifuged. Thereafter, 20 microliters of the supernatant is sampled, added with 1 ml of "GLUCOSE B TEST", a coloring reagent for the glucose oxidase method commercialized by Wako Pure Chemical Industries, Ltd., Osaka, Japan, incubated at 37° C. for 20 minutes for color development, and assayed for absorbance at 505 nm.

EXPERIMENT 2

α-D-Glucosyl-L-ascorbic Acid

EXPERIMENT 2(1)

Saccharide-transfer Reaction

In 100 parts by weight of 0.2M acetate buffer (pH 5.3) was dissolved 7.04 parts by weight of L-ascorbic acid, 12.8 parts by weight of maltose and 0.2 parts by weight of thiourea, and the solution was added with 0.5 units/g maltose of a partially-purified α-glucosidase specimen prepared by the method in Experiment 1, and allowed to react at 50° C. for 5 hours under light-shielding conditions. The reaction was suspended by adding 4 volumes of 1.06 w/v % metaphosphatic acid solution to the reaction mixture to inactivate the enzyme.

HPLC analysis of the reaction mixture revealed that about 30% of the starting L-ascorbic acid was converted into a saccharide derivative.

EXPERIMENT 2 (2)

Purification

The reaction mixture was then subjected to a gel filtration chromatography on a column of "Bio-Gel P-2", a gel product of Bio-Rad, Richmond, Calif., USA, using water for elution to recover an α-D-glucosyl-L-ascorbic acid-rich fraction which was then subjected to HPLC on "Shim-Pack ODS", a column product of Shimadzu Seisakusho Ltd., Kyoto, Japan, using 0.3% acetic acid for elution. The α-D-glucosyl-L-ascorbic acid-rich fraction was recovered, concentrated in vacuo and pulverized by lyophilization to obtain a high-purity α-D-glucosyl-L-ascorbic acid specimen, purity of 99.9%, in the yield of about 80% against the α-D-glucosyl-L-ascorbic acid in the reaction mixture.

EXPERIMENT 2 (3)

Physicochemical Properties

A typical α-glycosyl-L-ascorbic acid specimen, prepared by the method in Experiment 2(2), was determined for the following physicochemical properties.

Another typical α-glycosyl-L-ascorbic acid with a higher α-D-glucosyl group, obtained by the method in Example A-1, was characterized by as far as possible, and its properties are given in the brackets.

(1) Elemental analysis

Found; C=42.6%, H=5.36%

Calculated; E=42.3%, H=5.38%, N<0.01% (for chemical formula $C_{12}H_{18}O_{11}$)

(2) Molecular weight

FD mass spectrometric analysis with "M-80B", a mass spectrometry commercialized by Hitachi Ltd., Tokyo, Japan, revealed a $(M+H)^+$ peak at 339 (molecular weight for chemical formula $C_{12}H_{18}O_{11}$ is 338).

(3) uv-Absorption spectrum

Exhibiting an absorption peak at 260 nm when at pH 7.0, while exhibiting an absorption peak at 238 nm when at pH 2.0.

[Exhibiting substantially the same property]

(4) Infrared absorption spectrum

The KBr tablet method was used. The result was as shown in FIG. 1.

[Exhibiting substantially the same property]

(5) NMR spectrum

The nmr spectrum was determined with "JNM-GX400", an nmr spectrometry commercialized by Japan Electron Optics Laboratory Co., Ltd., Tokyo, Japan.

The solvent was $D_2O$, and the pH during the measurement was 2.8.

TSP (sodium 3-trimethyl-silylpropionate-2,2,3,3-$d_4$) was used as the internal standard.

$^1$H-NMR δppm (in $D_2O$);

3.50 (1H, dd, J=9.5 Hz, J=9.7 Hz)

3.56 (1H, dd, J=3.4 Hz, J=9.5 Hz)

3.75 (2H, d, J=6.4 Hz)

3.78 (2H, d, J=3.0 Hz)

3.86 (1H, dd, J=9.5 Hz, J=9.5 Hz)

4.02 (1H, dt, J=9.7 Hz, J=3.0 Hz )

4.08 (1H, td, J=6.4 Hz, J=1.5 Hz)

4.91 (1H, d, J=1.5 Hz)

5.52 (1H, d, J=3.4 Hz)

These data confirm that the alcohol group which is located at the number two carbon atom forms together with D-glucose a glucoside via an ether bond.

(5) Dissociation constant

The pKa is 3.0. Comparison of this to those for various derivatives of L-ascorbic acid in Table 1 in J. Jernow et al., Tetrahedron, Vol. 35, pp. 1,483–1,486 (1979) and in Table 2 in Pao-Wen Lu et al., *Journal of Agricultural Food Chemistry*, Vol. 32, pp. 21–28 (1984) suggests that in the substance of the invention, the alcohol group which is located at the number two carbon atom in L-ascorbic acid is responsible for the α-D-glucosyl bond, while the alcohol group which is located at the number three carbon atom is in free form.

(6) Methylation analysis

The substance was methylated by the method described in Pao-Wen Lu et al., *Journal of Agricultural Food and Chemistry*, Vol. 32, pp. 21–28 (1984) wherein L-ascorbic acid was methylated with diazomethane to predominantly form 3-O-methyl-L-ascorbic acid. Hydrolysis of the resultant led to the formation of 3-O-methyl-L-ascorbic acid and D-glucose as the predominant products.

The nmr spectrum, dissociation constant and methylation analysis suggest that the alcohol group which is located at the number two carbon atom forms with D-glucose an α-glucoside linkage via an ether bond.

(7) Solubility in solvents

Readily soluble in water, 0.1N sodium hydroxide and 0.1N acetic acid; soluble in methanol and ethanol; and insoluble in ether, benzene and chloroform.

[Exhibiting substantially the same property]

(8) Coloring reaction

Exhibiting no direct reducing activity, and not reducing and decoloring 2,6-dichlorophenolindophenol.

Negative to the 2,4-dinitrophenylhydrazine reaction.

Turning green on the anthrone-sulfuric acid reaction.

[Exhibiting substantially the same property]

(9) Stability (a) Hydrolyzable by α-glucosidase or by treatment with 1N hydrochloric acid at 100° C. for 5 minutes to form L-ascorbic acid and D-glucose at a molar ratio of 1:1.

[Hydrolyzable by glucoamylase to form 2-O-α-D-glucosyl-L-ascorbic acid and D-glucose]

(b) Unhydrolyzable by β-glucosidase.

[Exhibiting substantially the same property]

(c) 2-O-α-D-Glucosyl-L-ascorbic acid was compared respectively to the 6-O-α-D-glucosyl-L-ascorbic acid disclosed in Japanese Patent Publication No. 38,158/73, and L-ascorbic acid for their stability in aqueous solution. More particularly, each sample was adjusted to a concentration of 70 micromoles and to pH 7.0 or 2.0, placed in a cuvette, and measured for its absorbance at either 260 nm and pH 7.0 or at 245 nm and pH 2.0 while keeping the solution at 20 ° C. The remaining ratio (%) was calculated with the absorbance.

The results were as shown in Table I. As obvious from the results in Table I, unlike 6-O-α-D-glucosyl-L-ascorbic acid and L-ascorbic acid, 2-O-α-D-glucosyl-L-ascorbic acid is extremely stable in aqueous solution.

[Exhibiting substantially the same property as that of 2-O-α-D-glucosyl-L-ascorbic acid]

TABLE I

| pH | | Time (hour) | | | | |
|---|---|---|---|---|---|---|
| | | 0 | 0.25 | 0.5 | 1.0 | 21.0 |
| 7 | 2GAsA | 100% | 100% | 100% | 100% | 100% |
| | 6GAsA | 100% | 58% | 36% | 17% | 8% |
| | AsA | 100% | 47% | 20% | 8% | 2% |
| 2 | 2GAsA | 100% | 100% | 100% | 100% | 100% |
| | 6GAsA | 100% | 99% | 98% | 91% | 55% |
| | AsA | 100% | 99% | 97% | 87% | 10% |

Note: 2GAsA is the symbol for 2-O-α-D-glucosyl-L-ascorbic acid of the invention; 6GAsA, for 6-O-α-D-glucosyl-L-ascorbic acid as a control; and AsA, for L-ascorbic acid as one another control.

(10) Physiological activities (a) Reducing activity on cytochrome C

2-O-α-D-Glucosyl-L-ascorbic acid, 6-O-α-D-glucosyl-L-ascorbic acid and ascorbic acid were compared for their reducing activity on cytochrome C.

To a mixture of 0.5 ml of 0.2 mM EDTA in 0.1M potassium phosphate buffer <pH 7.8) and 0.1 ml of 0.1 mM cytochrome C was added an prescribed amount of water to give a final volume of 1 ml which was then added with 10 microliters of 10 mM of either sample, and determined for its change in absorbance at 550 nm and ambient temperature with a photospectrometry. The difference in absorbance (ΔA/minute/10 microliters) was determined with the initial reaction rate, and the reducing activity was estimated with the difference in absorbance.

As the result, it was confirmed that unlike 6-O-α-D-glucosyl-L-ascorbic acid and L-ascorbic acid, 2-O-α-D-glucosyl-L-ascorbic acid exhibited no reducing activity.

Also was confirmed that 2-O-α-D-glucosyl-L-ascorbic acid exhibited a reducing activity when hydrolyzed by an α-glucosidase specimen prepared by the method in Experiment 1.

(b) Collagenic activity

2-O-α-D-Glucosyl-L-ascorbic acid, 6-O-α-D-glucosyl-L-ascorbic acid and L-ascorbic acid were tested for their collagenic activity.

A human fibroblast cell, cell density of 7×10⁴ cells/plate, was cultured in Eagle's minimal essential medium supplemented with 10% FCS for 1 week, added with 4 μCi/ml ³H-proline, 20 μg/ml of β-aminopropionitrile and 0.25 mM of either sample, and cultured for an additional 24 hours. The resultant was then added with 10 w/v % trichloroacetic acid to recover the collagenous element in the culture, followed by lyophilization. The resultant specimen was dissolved, and the solution was adjusted to an appropriate pH, treated with a collagenase (Type III) at 37° C. for 90 minutes, and centrifuged. Collagenic activity was estimated by determining the radio activity in the supernatant.

As the result, it was confirmed that 2-O-α-D-glucosyl-L-ascorbic acid had the same collagenic activity as that of L-ascorbic acid.

Also was confirmed that 6-O-α-D-glucosyl-L-ascorbic acid was slightly inferior in collagenic activity to that of 2-O-α-D-glucosyl-L-ascorbic acid.

The above physicochemical properties confirm that the α-glycosyl-L-ascorbic acid exhibiting no direct reducing activity prepared in this Experiment has the chemical structure shown by the formula [III]:

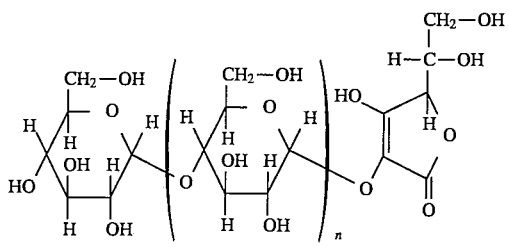

wherein n is an integer from 0 to 6.

2-O-α-D-Glucosyl-L-ascorbic acid, a typical α-glycosyl-L-ascorbic acid, has the chemical structure shown by the formula [IV]:

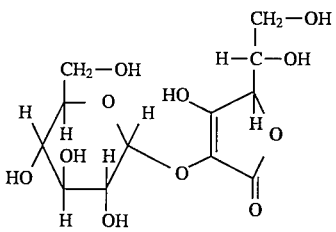

EXPERIMENT 3

Synthesis in vivo

Rats were orally administered with 1 g L-ascorbic acid and 500 mg maltose as in the form of 5 ml of 10 w/v % solution, and their blood was sampled at intervals and centrifuged. HPLC of the supernatants or plasmas confirmed that the peaks of α-D-glucosyl-L-ascorbic acid and a small amount of α-D-maltosyl-L-ascorbic acid appeared about 30 minutes after the administration, reached their maxima at 180 minutes, thereafter suddenly disappeared, and disappeared from blood for 360 minutes.

The substance which exhibited one of these peaks and corresponded to α-D-glucosyl-L-ascorbic acid as the predominant element was isolated and studied in detail, confirming that its physicochemical properties were identical to those of 2-O-α-D-glucosyl-L-ascorbic acid.

Accordingly, it would be concluded that α-glycosyl-L-ascorbic acid is highly safe because it is a biosubstance which is synthesized, metabolized and disappeared in vivo.

EXPERIMENT 4

Acute Toxicity

A high-purity α-D-glucosyl-L-ascorbic acid specimen, prepared by the method in Experiment 2(2), was orally administered to 7 week-old dd mice for acute toxicity test. As the result, no mouse died when administered with up to 5 g of the specimen, and higher dose was difficult.

These confirmed that the specimen was extremely low in toxicity. An α-glycosyl-L-ascorbic acid prepared by the method in Example A-1 was tested similarly as above to obtain the same result, confirming that the toxicity of this specimen was extremely low.

The following Examples A and Examples B will illustrate the α-glycosyl-L-ascorbic acid exhibiting no direct reducing activity and its uses respectively.

EXAMPLE A-1

α-Glycosyl-L-ascorbic Acid

Nine parts by weight of α-cyclodextrin was dissolved in 20 parts by weight of water by heating, and the solution was added with 3 parts by weight of L-ascorbic acid under reducing conditions, thereafter while keeping the solution at pH 5.5 and 60° C., added with 150 units/g α-cyclodextrin of cyclomaltodextrin glucanotransferase commercialized by Hayashibara Biochemical Laboratories, Inc., Okayama, Japan, and allowed to react for 40 hours. The reaction mixture was fed to "AQ-303 ODS" HPLC system, a product of Yamamura Chemical Laboratories Co., Ltd., Kyoto, Japan, equipped with "LC-6" column, a product of Shimadzu Seisakusho Ltd., Kyoto, Japan, and eluted with 0.1M $KH_2PO_4$-$H_3PO_4$ buffer (pH 2.0) at a flow rate of 0.5 ml/minute while monitoring with "MULT-340" detector system, a product of Japan Spectroscopic Co., Ltd., Tokyo, Japan. As the result, L-ascorbic acid appeared at a retension time of 9.5 minutes, while the newly formed α-D-glucosyl-L-ascorbic acid, α-D-maltosyl-L-ascorbic acid, α-D-maltotriosyl-L-ascorbic acid, α-D-maltotetraosyl-L-ascorbic acid, α-D-maltopentaosyl-L-ascorbic acid, α-D-maltohexaosyl-L-ascorbic acid and α-D-maltoheptaosyl-L-ascorbic acid appeared at respective retension time of 11.2 minutes, 15.7 minutes, 20.6 minutes, 24.9 minutes, 28.1 minutes, 32.1 minutes and 38.6 minutes. About 50% of the L-ascorbic acid was converted into α-glycosyl-L-ascorbic acid. Thereafter, the reaction mixture was heated to inactivate the remaining enzyme and filtered, and the filtrate was purified in accordance with the method in Experiment 2(2) with a slight modification to isolate particular α-glycosyl-L-ascorbic acid elements. The elements were then mixed, concentrated in vacuo and pulverized to obtain a powdery α-glycosyl-L-ascorbic acid product in the yield of about 90% against the starting ascorbic acid, on the dry solid basis (d.s.b.).

The product exhibits no direct reducing activity, but exhibits satisfactorily high stability and physiological activity. Thus, the product is favorably usable as a stabilizer, quality-improving agent, physiologically active agent and uv-absorbent in foods, beverages, pharmaceuticals for susceptive diseases and cosmetics, as well as in the agents directed to enrich vitamin C.

EXAMPLE A-2

α-Glycosyl-L-ascorbic Acid

Forty parts by weight of dextrin (DE about 6) was dissolved in 50 parts by weight of water by heating, and the solution was added with 13 parts by weight of L-ascorbic acid under reducing conditions, thereafter while keeping the solution at pH 5.6 and 65° C., added with 270 units/g dextrin of cyclomaltodextrin glucanotransferase, and allowed to react for 40 hours. After analyzing the reaction mixture by HPLC similarly as in Example A-1, about 65% of the L-ascorbic acid was converted into α-glycosyl-L-ascorbic acids such as α-D-glucosyl-L-ascorbic acid, α-D-maltosyl-L-ascorbic acid, α-D-maltotriosyl-L-ascorbic acid, α-D-maltotetraosyl-L-ascorbic acid, α-D-maltopentaosyl-L-ascorbic acid and α-D-maltohexaosyl-L-ascorbic acid similarly as in Example A-1. Thereafter, the reaction mixture was heated to inactivate the remaining enzyme and filtered, after which the filtrate was purified in usual manner by the decoloration with activated carbon, and concentrated to obtain a syrupy α-glycosyl-L-ascorbic acid product additionally containing α-glucosyl saccharides in the yield of about 90% against the weight of the starting materials, d.s.b.

The α-glycosyl-L-ascorbic acid in the product exhibits no direct reducing activity, but exhibits satisfactorily high stability and physiological activity. Thus, the product is favorably usable as a seasoning, moisture-retaining agent, quality-improving agent, physiologically active agent and uv-absorbent in foods, beverages, pharmaceuticals for susceptive diseases and cosmetics, as well as in agents directed to enrich vitamin C.

EXAMPLE A-3

2-O-α-D-Glucosyl-L-ascorbic Acid

One part by weight of a syrupy α-glycosyl-L-ascorbic acid product additionally containing α-glucosyl saccharides, prepared by the method in Example A-2 with a slight modification, was dissolved in 4 parts by weight of water, and the solution was added with 100 units/g syrup solid of glucoamylase (EC 3.2.1.3) commercialized by Toyobo Co., Ltd., Osaka, Japan, and allowed to react at 50° C. for 50 hours. HPLC analysis of the reaction mixture revealed that particular α-glycosyl-L-ascorbic acids were converted into 2-O-α-D-glucosyl-L-ascorbic acid.

Thereafter, the reaction mixture was heated to inactivate the remaining enzyme and filtered, and the filtrate was purified by the method in Experiment 2(2) with a slight modification to recover a 2-O-α-D-glucosyl-L-ascorbic acid-rich fraction which was then concentrated in vacuo and pulverized to obtain a high-purity 2-O-α-D-glucosyl-L-ascorbic acid, purity of 99% or higher, in the yield of about 80% against the starting L-ascorbic acid, d.s.b.

Characterization of the product confirmed that its physicochemical properties were substantially the same as those of the 2-O-α-D-glucosyl-L-ascorbic acid in Experiment 2(3).

The 2-O-α-D-glucosyl-L-ascorbic acid is favorably usable as a stabilizer, quality-improving agent, physiologically active agent, uv-absorbent, chemical and pharmaceutical material in foods, beverages, pharmaceuticals for susceptive diseases, cosmetics and reagents, as well as in agents directed to enrich vitamin C which exhibits no direct reducing activity, but exhibits satisfactorily high stability and physiological activity.

EXAMPLE A-4

α-Glycosyl-L-ascorbic Acid

Twenty parts by weight of dextrin (DE 18) was dissolved in 70 parts by weight of water by heating, and the solution was added with 10 parts by weight of L-ascorbic acid under reducing conditions, further added with 4 units/g dextrin of a partially-purified α-glucosidase prepared by the method in Experiment 1, and allowed to react at pH 5.0 and 50° C. for 8 hours under light-shielding conditions. The reaction mixture was purified, concentrated and pulverized by the method in Example A-2 with a slight modification to obtain a powdery product in the yield of about 90%.

The product contained about 10 w/w % α-glycosyl-L-ascorbic acid.

The α-glycosyl-L-ascorbic acid exhibits no direct reducing activity, but exhibits satisfactorily high stability and physiological activity. Thus, the product is favorably usable as a seasoning, moisture-retaining agent, quality-improving agent, physiologically active agent and uv-absorbent in foods, beverages, pharmaceuticals for susceptive diseases and cosmetics, as well as in agents directed to enrich vitamin C.

EXAMPLE A-5

α-Glycosyl-L-ascorbic Acid

Ten parts by weight of maltose was dissolved in 80 parts by weight of water by heating, and the solution was added with 10 parts by weight of L-ascorbic acid and 4 units/g maltose of a rice seed α-glucosidase commercialized by Sigma Chemical Co., Saint Louis, Miss., USA, and allowed to react at pH 6.0 and 45° C. for 6 hours under light-shielding conditions. The reaction mixture was purified, concentrated and pulverized by the method in Example A-2 with a slight modification to obtain a powdery product in the yield of about 90%. The product contained about 15% α-glycosyl-L-ascorbic acid.

The α-glycosyl-L-ascorbic acid in the product exhibits no direct reducing activity, exhibits satisfactorily high stability and physiological activity. Thus, the product is favorably usable as a sweetener, seasoning, moisture-retaining agent, quality-improving agent, physiologically active agent and uv-absorbent in foods, beverages, pharmaceuticals for susceptive diseases and cosmetics, as well as in agents directed to enrich vitamin C.

EXAMPLE A-6

α-Glycosyl-L-ascorbic Acid

EXAMPLE A-6(1)

Preparation of α-glucosidase

*Mucor javanicus* IFO 4570 was inoculated and cultivated at 30° C. for 44 hours under aeration-agitation conditions in 500 parts by weight of a liquid culture medium which contained water together with 4.0 w/v % maltose, 0.1 w/v % potassium phosphate monobasic, 0.1 w/v % ammonium nitrate, 0.05 w/v % magnesium sulfate, 0.05 w/v % potassium chloride, 0.2 w/v % polypeptone and 1 w/v % calcium carbonate which had been sterilized by heating and sterilely added to the water immediately before the inoculation. After completion of the culture, the mycelia was recovered and immobilized in usual manner.

EXAMPLE A-6(2)

Preparation of α-glycosyl-L-ascorbic Acid

Forty parts by weight of "SUNMALT®" a crystalline maltose commercialized by Hayashibara Co., Ltd., Okayama, Japan, was dissolved in 70 parts by weight of water by heating, and the solution was added with 10 parts by weight of L-ascorbic acid and 10 units/g maltose of an immobilized α-glucosidase prepared by the method in Example A-6(1) under light-shielding conditions, and allowed to react at pH 5.5 and 50° C. for 3 hours.

The reaction mixture was filtered to remove the immobilized α-glucosidase which was then reused in another reaction batch. After heating, the filtrate was purified, concentrated and pulverized by the method in Example A-2 with a slight modification to obtain a powdery product in the yield of about 95%.

The product contained about 7 w/w % α-glycosyl-L-ascorbic acid.

The α-glycosyl-L-ascorbic acid in the product exhibits no direct reducing activity, but exhibits satisfactorily high stability and physiological activity. Thus, the product is favorably usable as a sweetener, seasoning, moisture-retaining agent, quality-improving agent, physiologically active agent and uv-absorbent in foods, beverages, pharmaceuticals for susceptive diseases and cosmetics, as well as in agents directed to enrich vitamin C.

EXAMPLE B-1

Chewing Gum

Twenty-five parts by weight of gum base and 20 parts by weight of a powdery α-glycosyl-L-ascorbic acid obtained by the method in Example A-6 were kneaded at 60° C. with a mixer, and the mixture was added with 50 parts by weight of "MABIT®", an anhydrous crystalline maltitol commercialized by Hayashibara Shoji Inc., Okayama, Japan, 1.5 parts by weight of calcium phosphate and 0.1 part by weight of an L-menthol including β-cyclodextrin, and further mixed with a small amount of seasoning, rolled and cut to obtain the captioned product. The product is a vitamin C-enriched, low-cariogenic and low-caloric chewing gum.

EXAMPLE B-2

"Gyuhi (starch paste)"

One part by weight of waxy rice starch was mixed with 1.2 parts by weight of water, and the mixture was mixed to homogeneity with 1.5 parts by weight of sucrose, 0.7 parts by weight of "SUNMALT®", a crystalline β-maltose commercialized by Hayashibara Co., Ltd., Okayama, Japan, 0.5 parts by weight of a syrupy α-glycosyl-L-ascorbic acid obtained by the method in Example A-2 while gelatinizing by heating. Thereafter, the resultant was molded and packaged in usual manner to obtain "gyuhi".

The product is a vitamin C-enriched, Japanese-style confectionery with excellent flavor and biting properties, which looks like "kibi-dango (millet dumpling)". The product exhibits a long shelf life because its retrogradation is effectively suppressed.

EXAMPLE B-3

Mixed Sweetener

A mixed sweetener was obtained by mixing 100 parts by weight of honey, 50 parts by weight of isomerized sugar, 2 parts by weight of "kurozato (unrefined sugar)" and 1 part by weight of a high-purity 2-O-α-D-glucosyl-L-ascorbic acid powder obtained by the method in Example A-3.

The product is a vitamin C-enriched sweetener, and suitable for health food.

EXAMPLE B-4

Chocolate

Forty parts by weight of cacao paste, 10 parts by weight of cacao butter, 50 parts by weight of anhydrous crystalline maltitol and 1 part by weight of an α-glycosyl-L-ascorbic acid powder obtained by the method in Example A-1 were mixed to homogeneity, and the mixture was fed to a refiner to reduce the particle size, transferred to a conche, and kneaded therein at 50° C. for 2 days. In the kneading step, 0.5 parts by weight of lecithin was added and dispersed to homogeneity. Thereafter, the content was adjusted to 31° C. with a thermoregulator, and placed in a mold immediately before the solidification of the butter, deaerated with a vibrator, and solidified by passing it through a 10° C. cooling tunnel over a period of 20 minutes. The content was removed from the mold, and packaged to obtain the captioned product.

The product is free of hygroscopicity and excellent in color, gloss and texture, as well as smoothly melting in the mouth to exhibit a moderate and mild sweetness and flavor. The product is a vitamin C-enriched, low-cariogenic and low-caloric chocolate.

EXAMPLE B-5

Cream Filling

A cream filling was obtained by mixing in usual manner 1,200 parts by weight of "FINETOSE®", a crystalline α-maltose commercialized by Hayashibara Co., Ltd., Okayama, Japan, 1,000 parts by weight of shortening, 10 parts by weight of an α-glycosyl-L-ascorbic acid powder obtained by the method in Example A-2, 1 part by weight of lecithin, 1 part by weight of lemon oil and 1 part by weight of vanilla oil to homogeneity.

The product is a vitamin C-enriched cream filling which is excellent in taste, flavor, melting and biting properties, and the oxidation-of the fatty substances is effectively suppressed.

EXAMPLE B-6

Tablet

Twenty parts by weight of a high-purity 2-O-α-D-glucosyl-L-ascorbic acid powder obtained by the method in Example A-3 was mixed to homogeneity with 13 parts by weight of crystalline β-maltose, 4 parts by weight of cornstarch, 1 part by weight of rutin and 0.5 parts by weight of riboflavin, and the resultant was tableted to obtain the captioned product, 150 mg each.

The product is a stable and easily swallowable vitamin compound of vitamin C, vitamin P and vitamin $B_2$.

EXAMPLE B-7

Capsule

Ten parts by weight of calcium acetate monohydrate, 50 parts by weight of magnesium L-lactate trihydrate, 57 parts by weight of maltose, 20 parts by weight of an α-glycosyl-L-ascorbic acid powder obtained by the method in Example A-2, and 12 parts by weight of a γ-cyclodextrin inclusion compound containing 20% eicosapentaenoic acid were mixed to homogeneity, and the mixture was fed to a granulator, and then encapsulated in gelatine to obtain capsules, 150 mg each.

The product is favorably usable as a high-quality blood cholesterol lowering agent, immunopotentiator and skin-refining agent in preventive and remedy for susceptive diseases, as well as in foodstuffs directed to the maintenance and promotion of health.

EXAMPLE B-8

Ointment

One part by weight of sodium acetate trihydrate, 4 parts by weight of DL-calcium lactate and 10 parts by weight of glycerine were mixed to homogeneity, and the mixture was added to another mixture of 50 parts by weight of vaseline, 10 parts by weight of vegetable wax, 10 parts by weight of lanolin, 14.5 parts by weight of sesame oil, 1 part by weight of an α-glycosyl-L-ascorbic acid obtained by the method in Example A-4 and 0.5 parts by weight of peppermint oil, and mixed to homogeneity to obtain an ointment.

The product is favorably usable as a high-quality sunscreen agent, skin-refining agent, skin-whitening agent and promoter for healing injury and burn.

EXAMPLE B-9

Injection

A high-purity α-D-glucosyl-L-ascorbic acid powder obtained by the method in Experiment 2(2) was dissolved in water, neutralized and sterilely filtered in usual manner to obtain a pyrogen-free solution which was then distributed to 20 ml glass vials to give an α-D-glucosyl-L-ascorbic acid content of 500 mg, dried in vacuo and sealed to obtain the captioned product.

The product is intramuscularly and intravenously administrable alone or in combination with vitamins and minerals. The product requires no cold storage, and exhibits an excellently high solubility in saline when in use.

The product, which exhibits in vivo an about 2–10-fold longer residence time than L-ascorbic acid, is gradually hydrolyzed to release L-ascorbic acid which then elicits its inherent physiological activities.

Besides supplementing vitamin C, the product acts as an antioxidant to exert both activated oxygen-removing and lipoperoxide formation-inhibiting effects when hydrolyzed. Thus, the product is favorably usable in preventive and remedy for various susceptive diseases such as viral diseases, bacterial diseases, traumatic diseases, immunopathies, allergy, diabetes, cataract, circulatory diseases and malignant tumors.

EXAMPLE B-10

Injection

Six parts by weight of sodium chloride, 0.3 parts by weight of potassium chloride, 0.2 parts by weight of calcium chloride, 3.1 parts by weight of sodium lactate, 48 parts by weight of maltose and 2 parts by weight of a high-purity 2-O-α-D-glucosyl-L-ascorbic acid powder obtained by the method in Example A-3 were dissolved in 1,000 parts by weight of water, and sterilely filtered in usual manner, and 250 ml aliquots of the resultant pyrogen-free solution were distributed to sterilized plastic vessels to obtain the captioned product.

The product is usable in the supplement of vitamin C, calorie and minerals. The product acts as an antioxidant to exert both activated oxygen-removing and lipoperoxide formation-inhibiting effects when hydrolyzed. Thus, the product is favorably usable in the restoration of health during and before suffering from diseases, as well as in preventive and remedy for susceptive diseases such as viral diseases, bacterial diseases, traumatic diseases, immunopathies, allergy, diabetes, cataract, circulatory diseases and malignant tumors.

EXAMPLE B-11

Intubation Nutrient

Twenty four gram aliquots of a compound consisting of 20 parts by weight of crystalline α-maltose, 1.1 parts by weight of glycine, 0.18 parts by weight of sodium glutamate, 1.2 parts by weight of sodium chloride, 1 part by weight of citric acid, 0.4 parts by weight of calcium lactate, 0.1 part by weight of magnesium carbonate, 0.1 part by weight of an α-glycosyl-L-ascorbic acid powder obtained by the method in Example A-5, 0.01 part by weight of thyamine and 0.01 part by weight of riboflavin were packed in laminated aluminum bags, and heat-sealed to obtain the captioned product.

In use, one bag of the product is dissolved in about 300–500 ml of water, and the solution is favorably usable as an intubation nutrient directed to oral and parenteral administration to the nasal cavity, stomach and intestine.

EXAMPLE B-12

Bath Liquid

A bath liquid was obtained by mixing 21 parts of DL-sodium lactate, 8 parts by weight of sodium pyruvate, 5 parts by weight of an α-glycosyl-L-ascorbic acid powder obtained by the method in Example-A-1 and 40 parts by weight of ethanol with 26 parts by eight of refined water and appropriate amounts of coloring agent and flavoring agent.

The product is suitable for skin-refining agent and skin-whitening agent, which is diluted by 100–10,000-folds in bath water when in use. In this case, bath water is replaceable with cleansing liquid, astringent and moisture liquid.

EXAMPLE B-13

Milky Lotion

One half part by weight of polyoxyethylene behenyl ether, 1 part by weight of polyoxyethylene sorbitol tetraoleate, 1 part by weight of oil-soluble glyceryl monostearate, 0.5 parts by weight of pyruvic acid, 0.5 parts by weight of behenyl alcohol, 1 part by weight of avocado oil, 1 part by weight of a high-purity 2-O-α-D-glucosyl-L-ascorbic acid powder obtained by the method in Example A-3 and appropriate amounts of vitamin E and antiseptic were dissolved in usual manner by heating, and the solution was added with 1 part by weight of L-sodium lactate, 5 parts by weight of 1,3-butylene glycol, 0.1 part by weight of carboxyvinyl polymer and 85.3 parts by weight of refined water, emulsified with a homogenizer, added with an appropriate amount of flavoring agent, and mixed by stirring to obtained the captioned product.

The product is favorably usable as a high-quality sun-screen agent, skin-refining agent and skin-whitening agent.

EXAMPLE B-14

Cosmetic Cream

Two parts by weight of polyoxyethylene glycol monostearate, 5 parts by weight of self-emulsifying glycerine monostearate, 2 parts by weight of a high-purity 2-O-α-D-glucosyl-L-ascorbic acid powder obtained by the method in Example A-3, 1 part by weight of liquid paraffin, 10 parts by weight of glyceryl trioctanate and an appropriate amount of antiseptic were dissolved in usual manner by heating, and the mixture was added with 2 parts by weight of L-lactic acid, 5 parts by weight of 1,3-butylene glycol and 66 parts by weight of refined water, emulsified with a homogenizer, added with an appropriate amount of flavoring agent, and mixed by stirring to obtained the captioned product.

The product is favorably usable as a high-quality sun-screen cream, skin-refining agent and skin-whitening agent.

As described above, α-glycosyl-L-ascorbic acid, a novel substance of the invention, is free of direct reducing activity, superior in stability, and readily hydrolyzable in vivo to exhibit the antioxidant and physiological activities inherent to L-ascorbic acid. Furthermore, α-glycosyl-L-ascorbic acid is a highly safe substance because it is synthesized and metabolized in vivo.

α-Glycosyl-L-ascorbic acid is easily formed by a biochemical process wherein a saccharide-transferring enzyme is allowed to act on a solution containing L-ascorbic acid and an α-glucosyl saccharide. Thus, α-glycosyl-L-ascorbic acid is superior in economical efficiency, and commercializable with an ease.

Since the α-glycosyl-L-ascorbic acid exhibiting no direct reducing activity is satisfactorily high in stability and physiological activity, it is favorably usable as a stabilizer, quality-improving agent, antioxidant, physiologically active agent and uv-absorbent in foodstuffs including beverages and processed foods, preventive and remedies for susceptive diseases, and cosmetics including skin-refining agent and skin-whitening agent. Thus, the α-glycosyl-L-ascorbic acid of the invention has an extensive use, and is very significant in these industries.

We claim:

1. In a pharmaceutical composition containing a pharmaceutically-acceptable carrier and L-ascorbic acid as an effective ingredient for viral diseases, bacterial diseases, traumatic diseases, immunopathies, allergy, diabetes, cataract and malignant tumors, the improvement wherein said L-ascorbic acid is present in a form of an α-glycosyl-L-ascorbic acid which exhibits no direct reducing activity and has the chemical structure shown by the following formula:

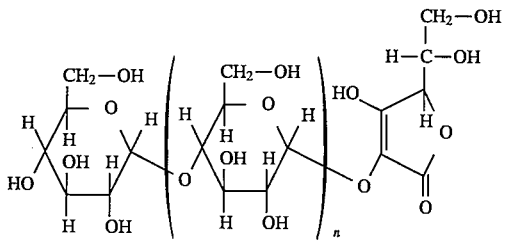

wherein n is an integer from 0 to 6, said composition containing at least 0.001 w/w% of said α-glycosyl-L-ascorbic acid.

2. The pharmaceutical composition of claim 1, wherein said α-glycosyl-n-ascorbic acid is 2-O-α-D-glucosyl-L-ascorbic acid having the formula:

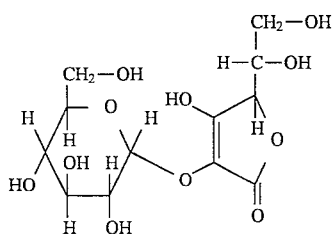

3. The pharmaceutical composition of claim 1, wherein said α-glycosyl-L-ascorbic acid is prepared by providing a solution which contains at least 1 w/v% L-ascorbic acid and an α-glycosyl saccharide in an amount of 0.5- to 30-fold higher than that of said L-ascorbic acid;

applying a saccharide-transferring enzyme to the solution containing said L-ascorbic acid and said α-glycosyl saccharide at a pH in the range of 3–9, and permitting said enzyme to act on said L-ascorbic acid and saccharide to form an α-glycosyl-L-ascorbic acid exhibiting no direct reducing activity; and recovering the α-glycosyl-L-ascorbic acid.

4. In a pharmaceutical composition containing L-ascorbic acid and a pharmaceutically acceptable excepient or carrier, the improvement wherein said L-ascorbic acid is in the form of α-glycosyl-L-ascorbic acid of the formula

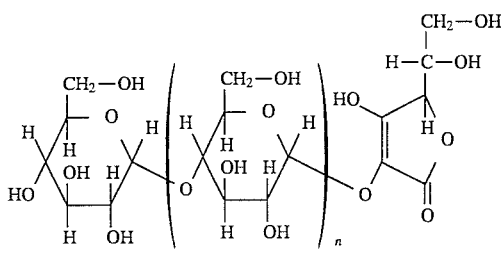

wherein n is an integer from 0 to 6.

5. A pharmaceutical composition for the administration to humans in need of vitamin C comprising at least 0.001 w/w% of α-glycosyl-L-ascorbic acid of the formula

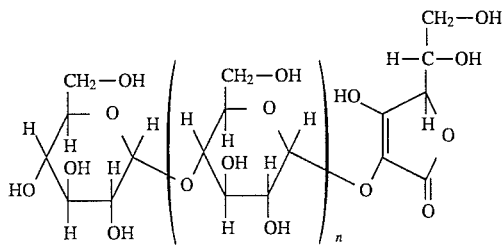

wherein n is an integer of from 0 to 6, and a pharmaceutically acceptable carrier.

* * * * *